(12) United States Patent
Yie et al.

(10) Patent No.: US 8,329,710 B2
(45) Date of Patent: Dec. 11, 2012

(54) METFORMIN FOLATE AND PREPARATION OF THE SAME

(75) Inventors: Hongping Yie, Huaibei (CN); Meg M. Sun, San Diego, CA (US); Zuolin Zhu, San Diego, CA (US)

(73) Assignee: Sino-Us Pficker Pharmaceuticals Co., Huaibei (CN)

( * ) Notice: Subject to any disclaimer, the term of this patent is extended or adjusted under 35 U.S.C. 154(b) by 417 days.

(21) Appl. No.: 12/515,657

(22) PCT Filed: May 11, 2007

(86) PCT No.: PCT/CN2007/070010
§ 371 (c)(1),
(2), (4) Date: Dec. 28, 2009

(87) PCT Pub. No.: WO2008/061456
PCT Pub. Date: May 29, 2008

(65) Prior Publication Data
US 2010/0105691 A1     Apr. 29, 2010

(30) Foreign Application Priority Data
Nov. 20, 2006   (CN) .......................... 2006 1 0149044

(51) Int. Cl.
*A61K 31/519* (2006.01)
(52) U.S. Cl. ................................... 514/262.1
(58) Field of Classification Search ............... 514/262.1; 544/258
See application file for complete search history.

(56) References Cited

FOREIGN PATENT DOCUMENTS
| | | | |
|---|---|---|---|
| CN | 1559394 A | 1/2005 | |
| WO | WO 01/56609 A1 | 8/2001 | |

OTHER PUBLICATIONS

Jordan, V. C. Nature Reviews: Drug Discovery, 2, 2003, 205-213.*
Hackam, et al. JAMA, 296(14), 2006, 1731-1732.*
International Search Report of PCT/CN2007/070010, dated Aug. 9, 2007.
Kilicdag et al. "Administration of B-group vitamins reduces circulating homocysteine in polycystic ovarian syndrome patients treated with metformin: a randomized trial." Human Reproduction, vol. 20(6), 2005, pp. 1521-1528.

* cited by examiner

*Primary Examiner* — Douglas M Willis
(74) *Attorney, Agent, or Firm* — Hamre, Schumann, Mueller & Larson, P.C.

(57) ABSTRACT

This disclosure is directed to compound having the formula (A) and a method of treatment using the compound. Compared with metformin, the disclosed compound has the same clinic curative effect, such as lowering blood sugar, curing poly-cystic ovary syndrome (PCOS), losing weight and so on, without resulting in the increase of homocysteine concentration, even with a little decrease of homocysteine concentration in some cases.

(A)

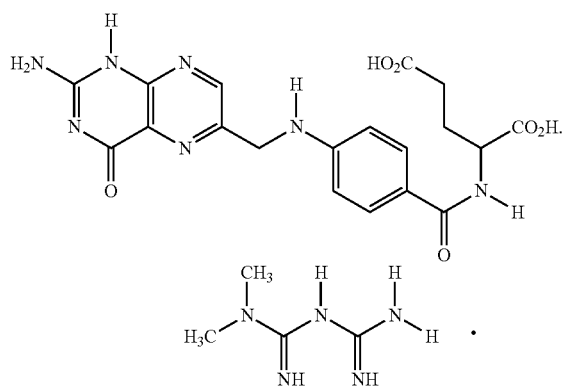

8 Claims, No Drawings

METFORMIN FOLATE AND PREPARATION OF THE SAME

CROSS-REFERENCE TO RELATED APPLICATIONS not applicable

STATEMENT REGARDING FEDERALLY SPONSORED RESEARCH OR DEVELOPMENT not applicable

THE NAMES OF THE PARTIES TO A JOINT RESEARCH AGREEMENT not applicable

INCORPORATION-BY-REFERENCE OF MATERIALS SUBMITTED ON A COMPACT DISC not applicable

FIELD

The present invention discloses a novel biguanide compound, more particularly, relates to a novel biguanide compound and the preparation of the same.

BACKGROUND

Currently, metformin is one of the widely used medicaments in many fields, the major pharmacological effects of which are lowering blood glucose, curing poly-cystic ovary syndrome (PCOS), and reducing weight. As an oral anti-hyperglycemia agent, metformin can improve the tolerance of a patient with Type II diabetes mellitus on glucose, and reducing basal and postprandial concentration of plasma glucose; the morbidity of poly-cystic ovary syndrome in women of childbearing ages is as high as 6%, and it is one of the leading causes of anovulation infertilitas, metformin can ameliorate menstrual disorder, induce spontaneous ovulation, promote the ovary response of PCOS patient more amenable to physiological condition, avoid the development of excessive ovarian follicle, and reducing complications caused by those conditions.

A typical metformin compound is metformin hydrochloride. However, through recent clinical application, the disadvantage has been found that the homocystein concentration in the patient is substantially increased after long-term use of metformin hydrochloride, and the high homocystein concentration is a primary factor of a number of heart-brain diseases. Similarly, the sulfate, phosphate, hydrobromide, hydriodate, and the like of metformin cannot overcome the above problem. Nevertheless, other severe adverse effects of metformin compounds have not been described, and metformin compounds are recognized as a medicament with excellent therapeutic effect.

Accordingly, there is a great need for metformin compounds which can be used over a long period and do not result in increase of the homocystein concentration.

SUMMARY

The object of the invention is to provide a novel metformin compound, known as folacin-metformin or metformin folate, represented by $C_{23}H_{30}N_{12}O_6$, as shown in formula (A).

Formula (A)

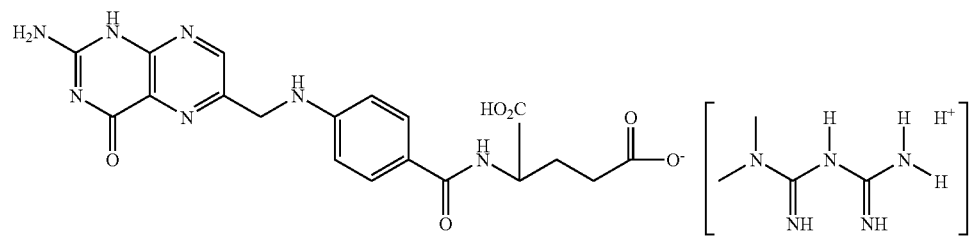

The above compound has the same clinical therapeutic effect as metformin hydrochloride, such as lowering blood glucose, curing poly-cystic ovary syndrome (PCOS), reducing weight, and the like. But no increase of the homocystein concentration in the patient was observed, even found slight decrease of the homocystein concentration in some cases.

The first aspect of the invention provided a compound of the following formula (A).

(A)

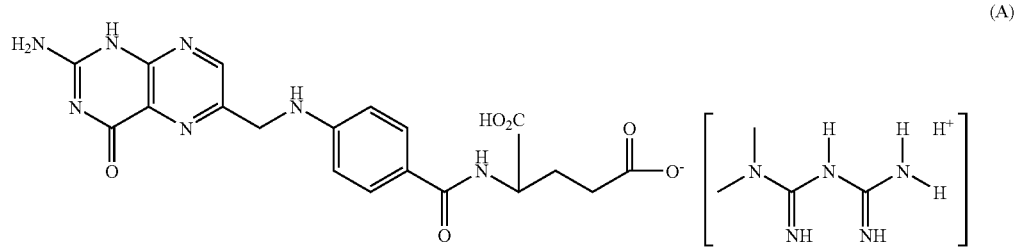

Another aspect of the invention provided the manufacturing process of the compound of formula (A), comprising the following steps:
(a) providing a free base of metformin;
(b) reacting the free base of metformin in step (a) with folacin to give folacin-metformin.

In an embodiment of the invention, the free base of metformin in step (a) is prepared by a method consisted of the following steps:
(A) providing an inorganic salt of metformin;
(B) reacting the inorganic salt of metformin in step (A) with a strong inorganic base to give the free base of metformin in step (A).

In one embodiment of the invention, the inorganic salt of metformin in step (A) is selected from the group consisting of metformin hydrochloride, sulfate, phosphate, hydrobromide, hydriodide, and the combination thereof, and/or
the strong inorganic base in step (B) is selected from the group consisting of sodium hydroxide, potassium hydroxide, calcium hydroxide, lithium hydroxide, rubidium hydroxide, and the combination thereof, and/or
the reaction temperature of step (B) is from 0 to 50° C., and/or
the reaction time of step (B) is from 0.5 to 1.5 hrs, and/or
the reaction of step (B) is performed in the presence of a solvent, the solvent is selected from the group consisting of water, C1-C4 alcohol, and the combination thereof, and/or
the equivalent ratio of the inorganic salt of metformin and the strong inorganic base is from 1:1.05 to 2, and/or
the reaction of step (B) is performed under nitrogen gas, and/or
the reaction of step (B)' is performed under refluxing.

Preferably, the temperature of step (B) is from 0 to 40° C.
Preferably, the C1-C4 alcohol is methanol, ethanol, and the combination thereof.

In a preferred embodiment of the invention, where the reaction of step (B) is performed in the presence of a solvent, the free base of metformin in step (B) is obtained by a method comprising any of the following steps:
(i) decompressing the solution obtained after the reaction to remove ⅔-⅘ volume of solvent, cooling, and filtering to give the free base of metformin in step (B) after precipitation, or
(ii) when the solvent is water, the solution obtained after the reaction is extracted by a low polar organic solvent to give the free base of metformin in step (B),
(iii) when the solvent is C1-C4 alcohol and combination thereof, the solution obtained after the reaction is cooled, then filtered, to give the free base of metformin in step (B).

Preferably, the free base of metformin obtained by step (i) and/or (iii) is further washed with alcoholic solvent to get the free base of metformin in alcohol, which is used in further steps. Said alcoholic solvent is preferably methanol, ethanol, and combination thereof.

Preferably, the low polar organic solvent described in step (ii) is selected from the group consisting of toluene, ethyl benzene, and combination thereof.

In a preferred embodiment of the invention, the equivalent ratio of the free base of metformin and folacin in step (b) is from 0.8 to 1, and/or
the reaction temperature of step (b) is from ambient temperature to 50° C., and/or
step (b) is performed in the presence of a solvent, the solvent is selected from the group consisting of C1-C4 alcohol and the combination thereof, and/or the reaction of step (b) is performed under nitrogen gas.

Preferably, the folacin-metformin resulted from step (b) is subjected to a reaction comprising:
(c) recrystallizing the folacin-metformin resulted from step (b) to give purified folacin-metformin; the recrystallizing solvent is selected from the group consisting of water, alcohol, and combination thereof.

Preferably, step (B) is performed in the present of a solvent, ⅔-⅘ volume of solvent is removed under reduced pressure and the solution is cooled to give the folacin-metformin solid; then the resulted folacin-metformin solid is recrystallized.

Another aspect of the invention provides a pharmaceutical composition comprising therapeutically effective amount of a compound of formula (A) and balanced amount of pharmaceutically acceptable carriers.

Still another aspect of the invention provides the use of a compound of formula (A) in preparing medicaments for lowering blood glucose, curing poly-cystic ovary syndrome, and/or reducing weight.

Another aspect of the invention provides a compound of formula (A) for preventing or treating hyperglycemia-related diseases, poly-cystic ovary syndrome, and/or obesity related diseases.

Preferably, the hyperglycemia-related disease is diabetes mellitus.

The invention further provides a method of using a compound of formula (A), the dose is 0.1-1000 mg/kg body weight, based on folacin-metformin.

Preferably, the dose is 78-1000 mg/kg body weight, based on folacin-metformin.

BRIEF DESCRIPTION OF THE DRAWINGS not applicable

DETAILED DESCRIPTION

The invention will be further illustrated in combination with the following specific examples. It should be appreciated that the examples are only for illustrating the invention, and not limiting the scope of the invention. The experimental methods whose particulars are not indicated in the examples are performed according to conventional conditions or the manufacture's recommending conditions.

As used herein, "strong inorganic base" refers to a basic inorganic material which can neutralize the inorganic salt of metformin. It may be a hydroxide comprising alkaline metal or alkaline earth metal, and it prefer alkaline metal hydroxide, such as sodium hydroxide, potassium hydroxide, calcium hydroxide, lithium hydroxide, rubidium hydroxide, and the combination thereof.

As used herein, "low polar organic solvent" refers to a polar organic solvent which can extract the free base of metformin from water. It may be alkyl benzene solvent, such as, selected from toluene, ethyl benzene, and combination thereof.

As used herein, "ambient temperature" refers to 10-30° C. of room temperature. Certainly, the ambient temperature can also be dependent on specific circumstances, which is, for example, 5-10, or 30-35° C.

Unless otherwise defined or illustrated, all the technical and scientific terms used herein have the same meaning as commonly understood by the skills in the art. Additionally, any method and material similar or equivalent to those described herein can be applied in the method of the invention.

Compound:

The compounds of the invention comprise all the corresponding pharmaceutically acceptable salts, hydrates, and isomers, which can be presented as racemic mixture, separate enantiomer, separate diastereoisomer, mixture of diastereoisomers, cis- or trans-isomer. All those isomers are predictable.

Particularly, the compound (A) of the invention comprises:

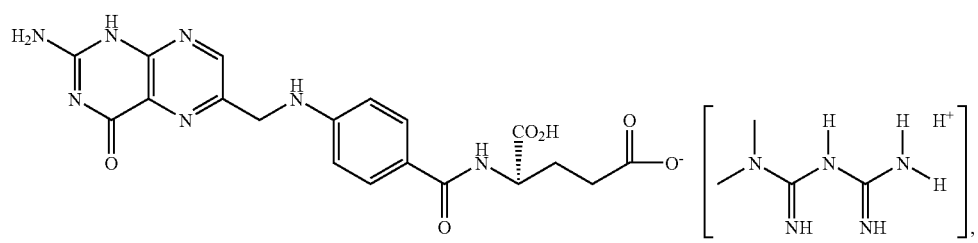

(A1)

and enantiomer (A2) of formula (A1), racemic mixture, or combination thereof.

Additionally, folacin described in the invention comprises various in vivo metabolic forms, such as tetrahydrofolate, and etc.

Preparation Methods:

The compound of the invention can be prepared by a multi-step process, comprising a first step of producing metformin by raw materials, cyanoguanide and dimethylamine; or it can also be directly prepared by the inorganic salt of metformin used as raw materials. The inorganic salts of metformin comprise metformin hydrochloride, sulfate, phosphate, hydrobromide, hydriodide, and the like. Large scale industrialized production can be achieved as soon as possible by a preparation method using metformin hydrochloride as raw material.

The method for preparing folacin-metformin using the inorganic salt of metformin as raw material is detailed below.

First, the free base of metformin is prepared from the organic salt of metformin. The reaction is performed under inert gas (e.g. argon). Typically, the material used to neutralize the organic salt of metformin is a strong inorganic base, such as calcium hydroxide, sodium hydroxide, potassium hydroxide, lithium hydroxide, or the combination thereof, in an amount of 1.05-2, preferably 1.1-2 eq. Water, C1-C4 alcohol (e.g. methanol, ethanol, or combination thereof), or mixture thereof in any ratio is used as solvent in the neutralization reaction. The reaction temperature is usually from 0-50° C., more usually 0-40° C. The reaction time should not be specifically limited, unless it limits the purpose of the invention, in particular, it could be, e.g., 0.5-1.5 hrs.

The reaction of inorganic salts of metformin and an inorganic base is performed in, e.g., aqueous solvent; the free base of metformin can be extracted by a low polar organic solvent, such as toluene, ethyl benzene, and the like. Of course, the solution obtained after most solvent is removed under reduced pressure, then, a low polar organic solvent, such as toluene, ethyl benzene, or combination thereof is used to extract the freebase of metformin. The reaction is performed in solvent, for example, C1-C4 alcohol (e.g. methanol, ethanol, or combination thereof in any ratio), and can be treated according to the following method: the solution obtained after the reaction is cooled, then filtered, and the solid is washed by fresh alcoholic solvent, to give the free base of metformin in alcohol; alternatively, the solution obtained after most solvent is removed under reduced pressure, then, a low polar organic solvent, such as toluene, ethyl benzene, or combination thereof is used to extract the freebase of metformin.

Secondly, folacin-metformin is prepared by the free base of metformin. The reaction is typically performed under inert gas (nitrogen gas) in alcoholic solvent (e.g. methanol, ethanol, or combination thereof). The free base of metformin is dissolved in alcohol, and 0.8-1 equivalent folacin is subsequently added, reacted to give a folacin-metformin solution.

The reaction time and temperature are not specifically limited, unless it limits the reaction. For example, the reaction temperature is from ambient temperature to 50° C.

Typically, the reaction product is recrystallized by using water, alcohol (e.g. C1-C4 alcohol), or combination thereof as solvent. The mixing ratio of water and alcohol is not specifically limited. For example, the folacin-metformin solution thus obtained after ⅔-⅘ volume of solvent is removed under reduced pressure, and cooled to give folacin-metformin solid, followed by recrystallizing the folacin-metformin solid obtained. The recrystallizing solvent can be water, methanol, ethanol, n-propanol, isopropanol, n-butanol, 2-butanol, and t-butanol, and the like. Particularly, for example, water, ethanol, or mixture thereof is used as the recrystallizing solvent.

The above synthetic method is only an example of part of the invented synthetic pathway. According to the above examples, the skills in the art can synthesize the compound of the invention by modifying different methods; otherwise, the skills in the art can synthesize the compound of the invention according to the existing well-known technologies. For example, metformin is prepared in accordance with other well-known technologies prior to synthesize folacin-metformin of the invention. As another example, the synthesized compound can be further purified by recrystallization, column chromatogram, high performance liquid chromatogram, and the like.

Composition:

As used herein, therapeutically effective amount refers to the amount which can result in any function or activity in human and/or animals, and is acceptable to human and/or animals. The "therapeutically effective amount" of the composition of the invention is from 0.1 to 1000 mg/kg body weight per day, based on folacin-metformin. The dose is preferably from 78 to 1000 mg/kg body weight per day, based on folacin-metformin. Any amount between the above range is the therapeutically effective amount of the invention. The "therapeutically effective amount" can be used alone or in combination to treat the related diseases. It can be understood by one of ordinary skill in the art that the amount in actual administration may be higher or lower than the above dose ranges.

The "therapeutically effective amount" and specific treatment strategy in a subject (e.g. mammal-human) may be dependent on many factors, including the pharmacological effect of the compound or the prodrug thereof, age, weight, general condition, gender, diet, administration time, susceptibility to diseases, progression of diseases of the subject, and the judgment of the clinical physician, and etc.

As used herein, "pharmaceutically acceptable carrier" is a carrier used for treating administration, which per se is not one of the essential active ingredients, and would not incur excess toxicity after application. Solid carriers are, for example, starch, lactose, ethylene glycol phosphate, microcrystalline cellulose, sucrose, and kaolin, and liquid carriers are, for example, sterilized water, polyethylene glycol, non-ionic surfactant, and edible oil (e.g. corn oil, peanut oil, and sesame oil), as long as they are suitable for the nature of the active ingredients and the desired specific administration mode.

Additionally, the pharmaceutical composition can be prepared by mixing with proper pharmaceutical additives, or diluting and dissolving in proper pharmaceutical additives. The additives mentioned are excipient, disintegrant, binder, lubricant, diluent, buffering agent, isotonizing agent, preservative, wetting agent, emulsifier, dispersing agent, stabilizer, solubilizer, and the like. The pharmaceutical composition is prepared by a conventional method.

Administration Mode:

The administration mode of the compound or the composition of the invention is oral. If necessary, it can also be administered through intravenous, intramuscular, subcutaneous, intranasal, and intrarectal routes, and among others. All the formulation suitable for metformin hydrochloride can be applied to folacin-metformin of the invention, e.g., the formulation is preferably solid formulation, such as tablet, granule, pill, and capsule, and the like.

The dosage regimen for treating a certain disease depends on multiple factors, including weight, age, gender, medical condition, severity of disease, administration route, and others.

The compound or the composition of the invention can be administered alone or in combination with other medicaments. Where the compound or the composition of the invention is used in combination with one or more of the above medicaments, the invention comprises the formulation being administered concurrently (either in a single dose, or in separate doses being administered in the same or different routes), and separate formulations being administered in different dosing intervals (in the same or different routes). The pharmaceutical composition comprising the compound (or the composition) of the invention and the above medicaments comprises the formulation administered as a single dose or separate doses, in order to use in combination as described above.

The inventor found, since the form of folacin-metformin does not lead to a raise of the concentration of homocysteine, even results in a decrease of the concentration thereof, the upper limit of the dosage is substantially elevated compared to metformin hydrochloride, which is of great benefit to lowering blood glucose, curing poly-cystic ovary syndrome (PCOS), and reducing weight.

Unless otherwise defined or illustrated, all the technical and scientific terms used herein have the same meaning as commonly understood by the skills in the art. Additionally, any method and material similar or equivalent to those described herein can be applied in the method of the invention.

EXAMPLE 1

Synthesis of Folacin-Metformin Compound

Under nitrogen protection, to a 500 mL flask were added 16.6 g (0.1 eq.) metformin hydrochloride solid and 100 mL ethanol solvent, and the reaction was stirred under mild heating until the solid was completely dissolved, then was cooled to ambient temperature. To the reaction was added 105 mL (0.105 eq.) 1N potassium hydroxide in methanol, and stirred while the reaction temperature was controlled at no more than 40° C. After 1 hr, about 150 mL solvent was removed under reduced pressure prior to slowly cool to about 10° C., then precipitation was initiated. The reaction was suction filtered, the precipitate was washed 2× by fresh ethanol, and the filtrates were combined to give the free base of metformin in ethanol.

Under nitrogen gas, 150 mL fresh ethanol was added to the free base of metformin in ethanol, and to the free base of metformin in ethanol was slowly added 42 g (0.095 eq.) folacin solid. At that time the temperature of the reaction mixture began to ascend. The reaction was stirred and the adding speed was controlled to keep the reaction temperature not exceeding 50° C. Stirring was continued until the solid was substantially dissolved. When new solid began to present, ⅔-⅘ volume of solvent was removed under reduced pressure, and the reaction was cooled to ambient temperature to give the crude product of folacin-metformin compound.

The product was recrystallized by water, to give white laminar crystalline. The crystalline was dried under vacuum at 40° C. to obtain about 36.5 g product with 64% yield.

Product m.p.: began to blacken at 245° C., and the temperature had not been corrected.

Element analysis result: calculated (%): Cm, 48.42; H, 5.30; N, 29.46. found (%): C, 48.99; H, 5.14; N, 28.93.

$^1$H-NMR (DMSO, 500 MHz, δ ppm): 8-2.3 (m, 12H), 2.39 (s, 6H), 3.8-4.6 (m, 6H), 6.6 (d, 2H), 7.6-8.1 (m, 5H), 10.4 (br, 1H);

$^{13}$C-NMR (DMSO, δ ppm): 25.8, 30.6, 34.3, 46.8, 54.7, 113.3, 122.5, 127.9, 133.1, 138.4, 143.7, 148.8, 151.0, 153.1, 155.2, 160.9, 167.7, 170.2, 173.4.

Animal Test

The female mice were induced to diabetic mice by streptozotocin (body weight 280-320 g), 6 animals in one group. The data in the table below represented the average of the values of six mice. Normal healthy mice were used as control group 1, control group 2, and control group 3. Control group 1 was administered folacin-metformin (350 mg/kg body weight), control group 2 was administered metformin hydrochloride (100 mg/kg body weight), and control group 3 was administered normal saline. Diabetic mice were divided into three groups, each group was fed folacin-metformin (350 mg/kg body weight), metformin hydrochloride (100 mg/kg body weight) and normal saline, separately. The test lasted for 10 days, and the blood glucose levels and the homocysteine concentrations were detected for all the mice by the end of the test.

On day 10 of the test, test mice were anaesthetized by i.p. injection of 65 mg/kg body weight of sodium pentobarbital, then collected blood sample from the abdominal aorta. Blood glucose levels were determined by a standard protocol (Methods of Enzymatic Analysis, Vol. 3, $2^{nd}$ ed. Verlag Chemie International, 1981, p1196-1201), and the homocysteine concentrations in the blood samples were determined using high performance liquid chromatograph according to the literature (Eur. J. Clin. Chem. Clin. Biochem. 1991, 29, 549-554). The results are presented in the following table 1.

TABLE 1

Animal test results with folacin-metformin vs. metformin hydrochloride

| | blood glucose level (mmol/L) | | homocystein concentration (μmol/L) | |
|---|---|---|---|---|
| | Before use | After use | Before use | After use |
| Control group 1: folacin-metformin | 7.3 ± 0.9 | 7.2 ± 1.2 | 9.9 ± 1.2 | 9.3 ± 1.1 |
| Control group 2: metformin hydrochloride | 7.5 ± 1.3 | 7.4 ± 1.7 | 9.8 ± 1.4 | 12.3 ± 1.3 |
| Control group 3: normal saline | 7.3 ± 0.9 | 7.2 ± 1.2 | 9.8 ± 1.1 | 9.9 ± 1.2 |
| Diabetic mice group 1: folacin-metformin | 18.7 ± 2.9 | 7.4 ± 1.7 | 9.3 ± 1.1 | 8.9 ± 0.9 |
| Diabetic mice group 2: metformin hydrochloride | 18.3 ± 2.1 | 7.6 ± 1.4 | 9.1 ± 1.1 | 10.9 ± 1.2 |
| Diabetic mice group 3: normal saline | 18.5 ± 2.3 | 34.6 ± 3.4 | 8.9 ± 1.3 | 9.3 ± 1.1 |

Result:

1. For the capacity of lowering blood glucose, there is no difference between folacin-metformin and metformin hydrochloride;

2. For healthy mice, folacin-metformin has no effect on the blood glucose level;

3. For healthy mice, folacin-metformin has a slight lowering effect on the blood homocysteine concentration, and metformin hydrochloride can substantially increase said concentration;

4. For diabetic mice, while lowering the blood glucose, folacin-metformin does not increase the homocysteine concentration, but metformin hydrochloride does.

SEQUENCE LISTING not applicable

We claim:

1. A compound of formula (A):

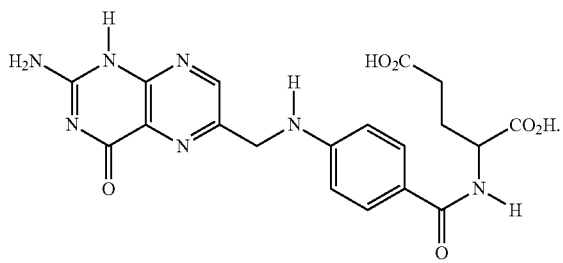

(A)

-continued

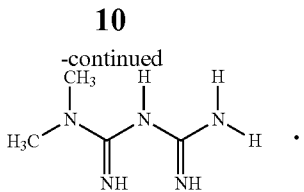

2. A pharmaceutical composition, comprising a therapeutically effective amount of a compound of formula (A) of claim 1 and a pharmaceutically acceptable carrier.

3. A method for preparing the compound of formula (A) of claim 1, comprising the following steps:
  (a) providing a free base of metformin, and
  (b) reacting the free base of metformin in step (a) with folic acid to give the folic acid salt of metformin.

4. The method of claim 3, wherein
  the equivalent ratio of the free base of metformin and folic acid in step (b) is from 0.8 to 1, and/or
  the reaction temperature of step (b) is from ambient temperature to 50° C., and/or
  step (b) is performed in the presence of a solvent, and the solvent is a C1-C4 alcohol or a mixture thereof, and/or
  the reaction of step (b) is performed under nitrogen protection.

5. A method for preparing the compound of formula (A) of claim 1, comprising the following steps:
  (1) providing an inorganic salt of metformin;
  (2) reacting the inorganic salt of metformin in step (1) with a strong inorganic base so as to give a free base of metformin; and
  (3) reacting the free base of metformin in step (2) with folic acid to give the folic acid salt of metformin.

6. The method of claim 5, wherein
  the inorganic salt of metformin in step (1) is selected from the group consisting of metformin hydrochloride, sulfate, phosphate, hydrobromide, hydriodide, and a combination thereof, and/or
  the strong inorganic base in step (2) is selected from the group consisting of sodium hydroxide, potassium hydroxide, calcium hydroxide, lithium hydroxide, rubidium hydroxide, and a combination thereof, and/or
  the reaction temperature of step (2) is from 0 to 50° C., and/or
  the reaction time of step (2) is from 0.5 to 1.5 hrs, and/or
  the reaction of step (2) is performed in the presence of a solvent, and the solvent is selected from the group consisting of water, a C1-C4 alcohol, and a combination thereof, and/or
  the equivalent ratio of the inorganic salt of metformin and the strong inorganic base in step (2) is from 1:1.05 to 2, and/or
  the reaction of step (2) is performed under nitrogen protection, and/or
  the reaction of step (2) is performed under refluxing.

7. A method of lowering blood glucose, treating polycystic ovary syndrome, treating diabetes mellitus and/or reducing weight, comprising administering an amount of the compound of formula (A) in accordance with claim 1 to a subject in need thereof.

8. The method of claim 7, wherein the amount administered to the subject is 0.1-1000 mg/kg body weight, based on the folic acid salt of metformin.

* * * * *